(12) United States Patent
Lamers et al.

(10) Patent No.: US 7,715,699 B2
(45) Date of Patent: May 11, 2010

(54) ELECTRICALLY ADDRESSABLE LIQUID DISPENSER

(75) Inventors: Kristina L. Lamers, Fort Collins, CO (US); Patrick Chiang, Sacramento, CA (US); Roger Flynn, Mountain View, CA (US); Yang-ren Rau, Hsinchu (TW); Beth L. Pruitt, San Francisco, CA (US); Aikaterina Ioakeimidi, San Francisco, CA (US)

(73) Assignee: Avago Technologies Wireless IP (Singapore) Pte. Ltd., Singapore (SG)

( * ) Notice: Subject to any disclaimer, the term of this patent is extended or adjusted under 35 U.S.C. 154(b) by 867 days.

(21) Appl. No.: 11/502,276

(22) Filed: Aug. 10, 2006

(65) Prior Publication Data
US 2008/0050102 A1    Feb. 28, 2008

(51) Int. Cl.
*A01G 13/06* (2006.01)
(52) U.S. Cl. .................................. 392/386; 392/394
(58) Field of Classification Search ........................ None
See application file for complete search history.

(56) References Cited

U.S. PATENT DOCUMENTS

| | | | |
|---|---|---|---|
| 4,882,245 A | | 11/1989 | Gelorme et al. |
| 5,644,342 A | * | 7/1997 | Argyres ........................ 347/12 |
| 6,390,453 B1 | * | 5/2002 | Frederickson et al. .......... 261/26 |
| 6,712,287 B1 | * | 3/2004 | Le Pesant et al. .............. 239/67 |
| 6,932,502 B2 | * | 8/2005 | Childers et al. ........... 366/152.1 |
| 7,310,539 B2 | * | 12/2007 | Chiang et al. ................ 455/567 |
| 2002/0022261 A1 | * | 2/2002 | Anderson et al. ......... 435/287.2 |
| 2002/0176802 A1 | * | 11/2002 | Chung et al. ................. 422/100 |
| 2004/0022677 A1 | * | 2/2004 | Wohlstadter et al. ........... 422/52 |
| 2004/0214056 A1 | * | 10/2004 | Gore ............................ 429/20 |
| 2004/0235430 A1 | * | 11/2004 | Ma et al. .................... 455/90.1 |
| 2005/0258133 A9 | * | 11/2005 | Maynard ........................ 216/2 |
| 2006/0037970 A1 | * | 2/2006 | Fazzio et al. .............. 222/145.1 |
| 2007/0245559 A1 | * | 10/2007 | Feinn et al. ................. 29/890.1 |
| 2008/0035207 A1 | * | 2/2008 | Lamers et al. ................. 137/67 |

* cited by examiner

*Primary Examiner*—Thor S Campbell (57) ABSTRACT

An electrically actuated liquid dispenser, an electrically addressable liquid dispenser and an electronic device are described.

20 Claims, 8 Drawing Sheets

| HEATER RESISTANCE (Ohms) | PRESSURE (psi) | VOLTAGE (V) | POWER (W)* ELECTROMIGRATION NOT CONSIDERED | RESULT |
|---|---|---|---|---|
| 21 | 90 | 2 | 0.19047 | CRACKED AND LIQUID CAME OUT UV AREA |
| 7 | 30 | 5 | 3.571428 | BLEW WELL COVER AWAY |
| 6 | 20 | 5.5 | 5.041666 | BLEW WELL COVER AWAY |
| 7.9 | 30 | 5.5 | 3.829113 | BLEW WELL COVER AWAY |

FIG. 5

| | PERIMETER (4*LENGTH) (μm) | HEATER METAL WIDTH (μm) | # OF SQUARES | RESISTANCE (OHMS) | APPLIED CURRENT (A) (V=1.5V) | APPLIED CURRENT (A) (V=0.5V) | POWER (W) (V=0.5V) |
|---|---|---|---|---|---|---|---|
| 1μm THICK Au (RESISTIVITY = 0.02 Ohms/sq) | 400 | 10 | 40 | 0.8 | 1.875 | 0.63 | 0.32 |
| 0.5μm THICK Au (RESISTIVITY = 0.04 Ohms/sq) | 400 | 10 | 40 | 1.6 | 0.94 | 0.31 | 0.156 |
| 0.5μm THICK Al (RESISTIVITY = 0.05 Ohms/sq) | 400 | 10 | 40 | 2 | 0.94 | 0.31 | 0.156 |

HEATER RESISTANCE R (Ω) = (P/W) *ο

ELECTRICALLY ADDRESSABLE LIQUID DISPENSER

BACKGROUND

Portable electronic devices continue to increase and improve in both form and function. For example, mobile phones often include a video function in addition to their audio function. This video function ranges from a basic display to a video recorder. As such, the human senses of hearing and seeing are engaged by many portable electronic devices. However, the olfactory sense is normally not engaged through the use of many known electronic devices.

While the use of scents may be beneficial to the user's experience, there remains the ever-increasing desire for reductions in size and cost of many portable electronic devices. As such, the addition of many known scent dispensing devices is not feasible.

What is needed, therefore, is an apparatus that overcomes at least the shortcomings described above.

SUMMARY

In accordance with an illustrative embodiment, an electrically actuated liquid dispenser includes a reservoir having a first layer disposed over a first opening and a second layer disposed over a second opening. The dispenser also includes a liquid material disposed in the reservoir; a heating element disposed over at least a portion of the first layer disposed over the first opening; and a pressure applicator disposed over at least a portion of the second layer disposed over the second opening. The heating element is adapted to mechanically weaken the portion of the first layer causing the first layer to break and to release the liquid material under pressure.

In accordance with another illustrative embodiment, an electrically addressable liquid dispenser includes a plurality of reservoirs, each reservoir having a first layer disposed over a first opening and a second layer disposed over a second opening. The dispenser also includes a liquid material disposed in each of the reservoirs; a plurality of heating elements, each heating element being disposed over a respective one of the first openings and in being contact with at least a portion of the first layer disposed over the respective first openings; and a pressure applicator disposed over each of the second openings and being in contact with the second layer.

In yet another illustrative embodiment, a portable electronic device includes the electrically addressable liquid dispenser. The dispenser includes: a plurality of reservoirs, each reservoir having a first layer disposed over a first opening and a second layer disposed over a second opening; a liquid material disposed in each of the reservoirs; a plurality of heating elements, each heating element being disposed over a respective one of the first openings and in being contact with at least a portion of the first layer disposed over the respective first openings; and a pressure applicator disposed over each of the second openings and being in contact with the second layer.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DEFINED TERMINOLOGY

The terms 'a' or 'an', as used herein are defined as one or more than one.

The term 'plurality' as used herein is defined as two or more than two.

DETAILED DESCRIPTION

In the following detailed description, for purposes of explanation and not limitation, specific details are set forth in order to provide a thorough understanding of example embodiments according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of apparati, methods and materials known to one of ordinary skill in the art may be omitted so as to not obscure the description of the example embodiments. Such methods and apparati are clearly within the scope of the present teachings.

Figure 1:
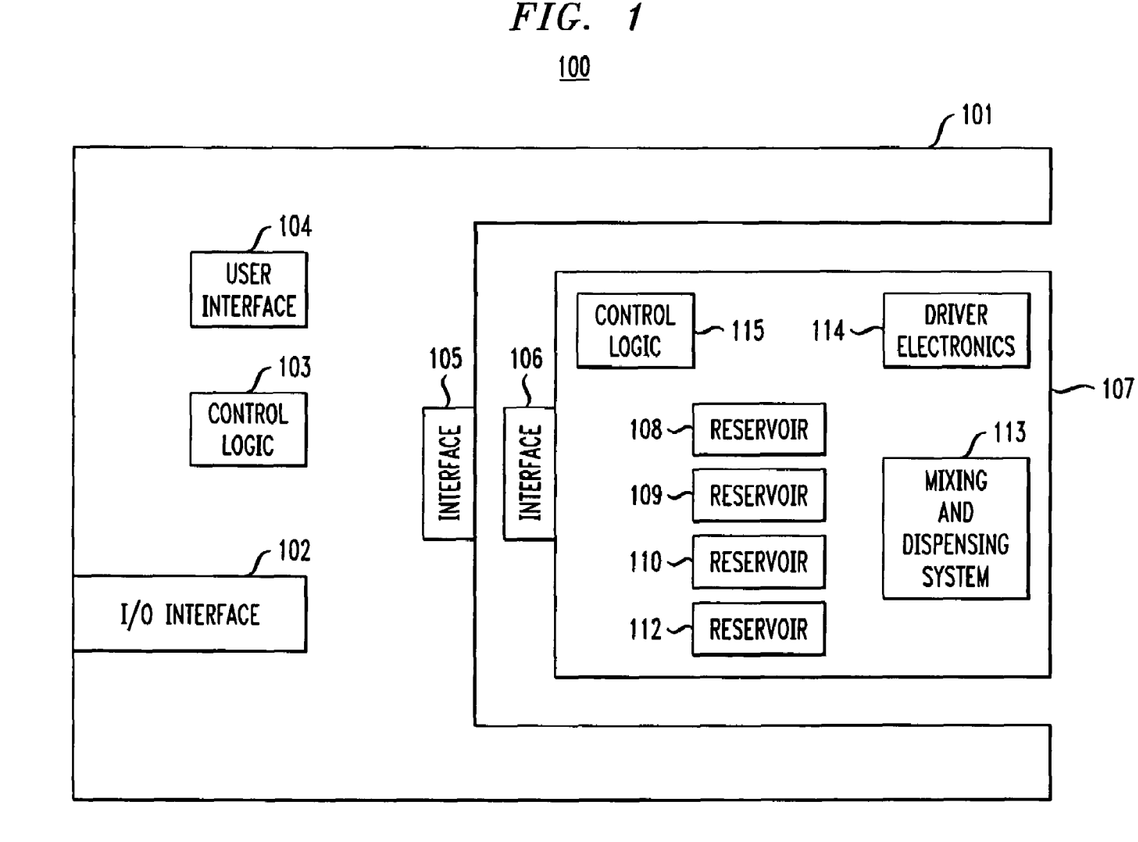
FIG. 1 is a conceptual block diagram of a portable electronic device in accordance with an illustrative embodiment.

FIG. 1 depicts a conceptual block diagram of a portable electronic device 100 in accordance with an illustrative embodiment. The device 100 may be a mobile (cellular) telephone, a personal digital assistant, a portable computer, a portable video player, a portable music player or a portable gaming device or a combination of one or more of these devices. It is emphasized that the noted devices are merely illustrative and that other devices within the purview of one of ordinary skill in the art are contemplated. Moreover, while the present description concentrates mainly on portable devices, the present teachings contemplate applications in traditionally non-portable devices such as home theatre; and traditionally non-electronic devices, such as the passenger compartment of an automobile. Again, this is merely illustrative and in no way limiting of the applications of the present teachings.

The device 100 includes a body 101 that includes many of the components required for its function. These include an input/output interface 102, a controller/control logic 103 and a user interface 104.

The I/O interface 102 provides for communications with other devices or systems (not shown). For example, the I/O interface 102 may be a wireless interface such as those used in mobile phones and PDAs. The I/O interface 102 may also include any other type of I/O interface such as infrared or wireline interfaces.

The control logic 103 of the device 100 supports operation of a dispenser module 107. The control logic 103 may include hardware, software, firmware or any combination thereof. The control logic 103 may be embodied as software code. Although the control logic 103 is shown as a separate functional element from the processing system for description purposes, the control logic 103 may be integrated within the processing system of the hand-held device.

The interface 104 allows a user to control the hand-held device and may include any type of user interface, for example, a display screen, a keypad, a touch screen, a pen-based system, a voice activated system, or any combination thereof. As will be appreciated, the interface 104 may be adapted to allow the user to engage the module 107 and the selected release of liquid therefrom.

The body 101 also includes an interface 105 adapted to connect to another interface 106 disposed on a liquid dispenser module 107. The interfaces 105, 106 are compatible and allow communications between the body 101 and the dispenser module 107. In particular, when connected to the interface 105 of the body 101, the interface 106 of the liquid dispenser module 107 allows control signals to be communicated between the body 101 and the dispenser module 107. In an embodiment, the interfaces 105, 106 are standard interfaces such as USB, MMC, RS-MMC, PCMCIA, Compact Flash, Memory Stick, Secure Digital, Firewire, PCI, IDE, ATA, or serial ATA.

Providing the liquid dispenser module 107 with a standard interface allows the module 107 to be compatible with a variety of hand-held devices that use the same standard interface and will enable the module 107 to be easily adopted by users of hand-held devices.

While representative embodiments are drawn to electrical interfacing and actuating, the present teachings contemplate that both the interface between the body 101 and the liquid dispenser module 107 and the actuation of the liquid dispenser module could be mechanical instead of or in addition to electrical.

The dispenser module 107 includes a plurality of reservoirs 108-112, which are described in more detail herein. The reservoirs 105-112 are adapted to contain liquid material under pressure. The liquid material may be a scent such as a perfume or other scent. In illustrative embodiments described more fully herein, the scent material may include approximately 20% scent oil and approximately 80% alcohol. It is noted that other fluids, besides liquids may be disposed in the reservoirs 108-112. In the interest of simplicity of description, liquids are described. However, other fluids within the purview of one of ordinary skill in the art are contemplated for use in conjunction with the illustrative embodiments.

The reservoirs 108-112 selectively provide liquid to a mixing and dispensing system 113. The system 113 includes channels (not shown) adapted to receive the liquids from the respective reservoirs 108-112 and to provide the liquid to the ambient via a nozzle or similarly suitable orifice. In addition, the system 113 is adapted to mix the selected liquids prior to dispensing, allowing the user to create mixtures of scents as desired in a customized fashion.

The liquid dispenser module 107 includes driver electronics 114 that are useful in dispensing the liquid materials. The driver electronics 114 are dependent on the dispense technique that is used and may be as simple as a potential difference (i.e., a voltage drop) or as complicated as an analog, a digital, or a mixed signal device/circuit that generates a signal waveform as either a current or voltage. As described more fully herein, heating elements are actuated by the driver electronics 114 to release the liquid materials under pressure to the mixing and dispensing system 113.

It is emphasized that pressure actuation described in conjunction with the representative embodiments is but one illustrative method of providing the liquid material. Alternatively, the pumping actuation may be effected using other devices or mechanisms. For example, piezoelectric, electro-osmotic, and/or thermoresistive devices and mechanisms may be used.

The dispenser module 107 optionally includes a control logic 115 to process control signals that are received from the body 101. The control logic 115 may include specialized functionality that is difficult or impractical to incorporate into the body 101. An example of the control logic includes pre-programmed dispensing functionality such as preprogrammed dispensing characteristics (e.g., liquid stream, spray, timed dispensing, and similar functionality).

Figure 2A:
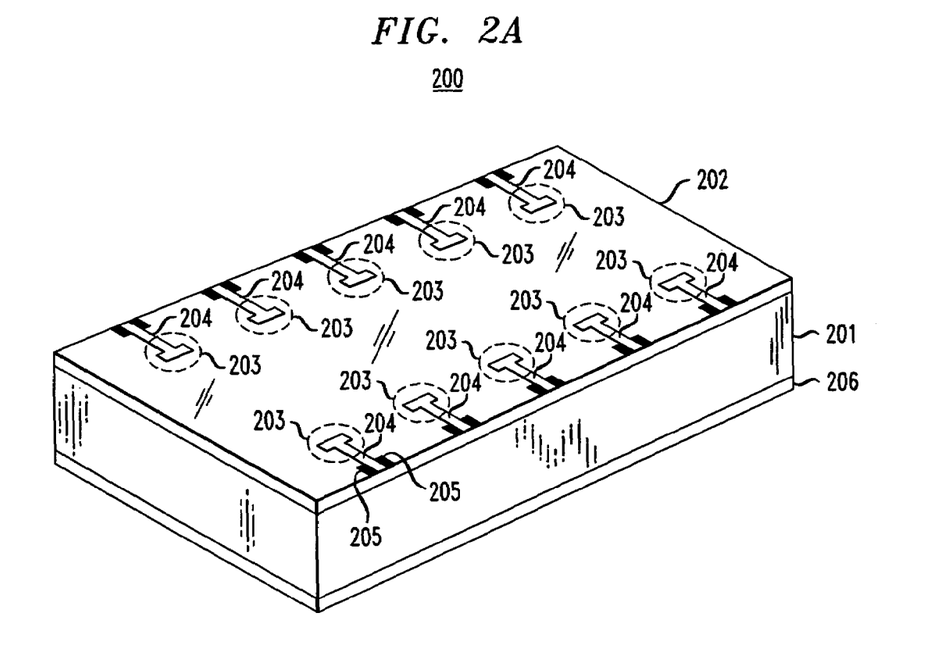
FIG. 2A is a perspective view of an electrically actuated liquid dispenser in accordance with an illustrative embodiment.

FIG. 2A is a perspective view of an electrically actuated liquid dispenser 200 in accordance with an illustrative embodiment. The dispenser 200 may include the components described in connection with the dispenser module 107, or may be a component of the module 107.

The dispenser 200 includes a substrate 201, which may be semiconductor (e.g., silicon), glass, plastic or other material adapted to micromachining and other desirable processing. In addition, and for reasons described in greater detail herein, the material of the substrate 201 is beneficially substantially hydrophilic to prevent absorption of oil in the liquid material. The substrate includes a first layer 202 disposed over a first side and a second layer 206 disposed over a second side. The second layer 206 is described in connection with FIG. 2C.

In a representative embodiment, the first layer 202 is a negative photoresist such as commercially available SU-8 polymer, described in U.S. Pat. No. 4,882,245, the disclosure of which is specifically incorporated herein by reference. It is noted that the first layer 202 is depicted as being transparent to facilitate description of the present embodiment. Notably, when a layer of SU-8 having a thickness of approximately 10 um or less is used for the first layer 202, it is fairly transparent. However, in other embodiments the first layer 202 is not necessarily transparent.

Shown by dashed lines, a plurality of first openings 203 is provided in the substrate 201. In the presently described embodiment, the openings 203 are substantially circular and are at one end of a cylindrical reservoir provided in the substrate 201. The reservoirs may be one or more of the reservoirs 108-112 described in connection with FIG. 1. It is emphasized that circular openings and cylindrical reservoirs are not essential and that other-shaped openings and reservoirs are contemplated.

A plurality of heating units 204 are disposed over the first layer 202, with one heating unit 204 being disposed over each of the openings 203. In an embodiment described more fully herein, the heating units 204 cause a mechanically weakened portion of the first layer 204 over the opening 203 to break and release liquid under pressure from its reservoir. Moreover, the heating units include pads 205 that are connected to the driver electronics 114, which selectively provide current to the pads 205 to cause the heating units to actuate. As will be appreciated, the selective actuation provides an electrically addressable liquid dispenser.

As alluded to previously, the actuation to release the liquid material from the reservoirs may be other than electrical. For example, rather than the electrical heating elements 204, a mechanical puncture mechanism may be used to release the liquid material.

Figure 2B:
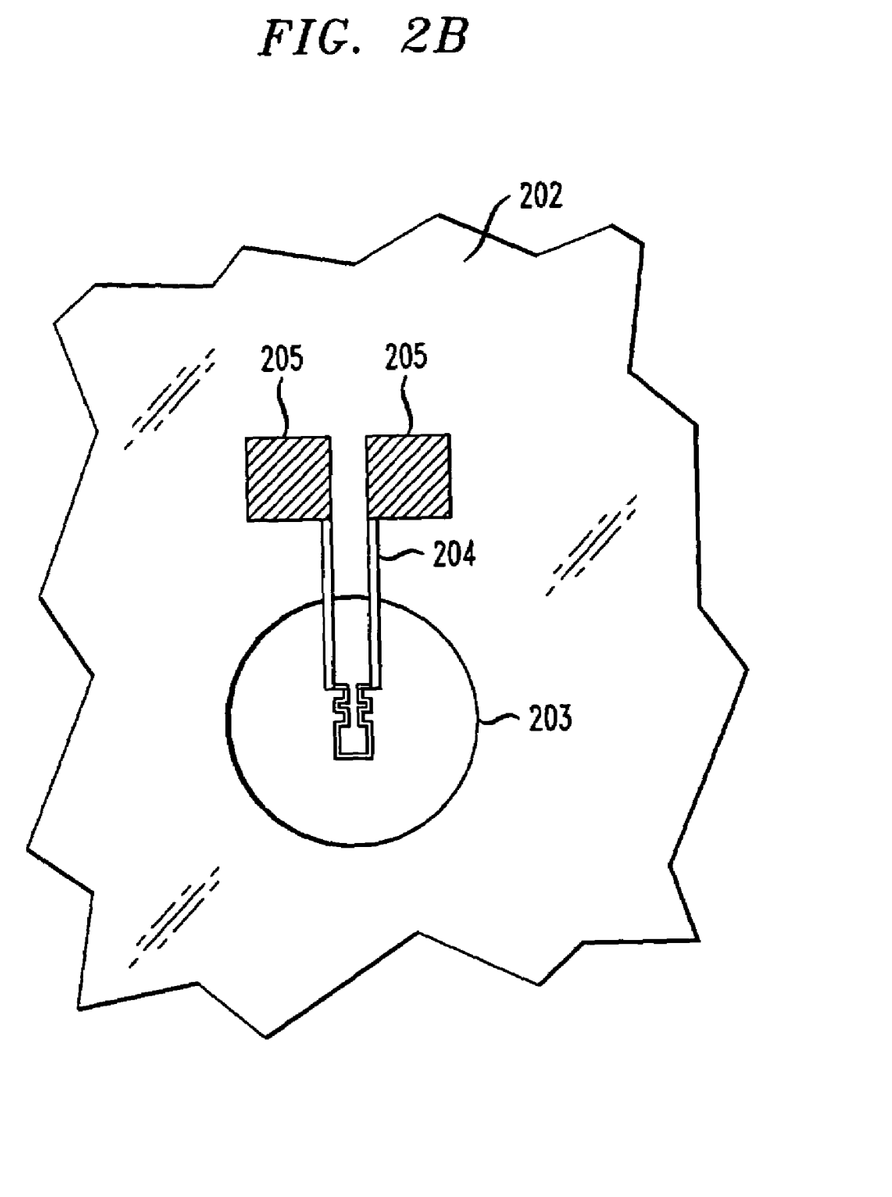
FIG. 2B is a perspective view of a heating element in accordance with an illustrative embodiment.

FIG. 2B is an enlarged view of one of the heating units 204 disposed over the first layer 202 and the first opening 203. In an illustrative embodiment, the heating units 204 are resistive elements comprising metal traces that are connected to the driver electronics 114 by pads 205. The application of current to the pads 205 causes the heating unit 204 to heat the portion of the first layer 202 disposed over the opening 203 and can cause the layer to break. As described more fully herein, the liquid material in the reservoir of the first opening 203 is under pressure and is ejected from the first opening 203.

Figure 2C:
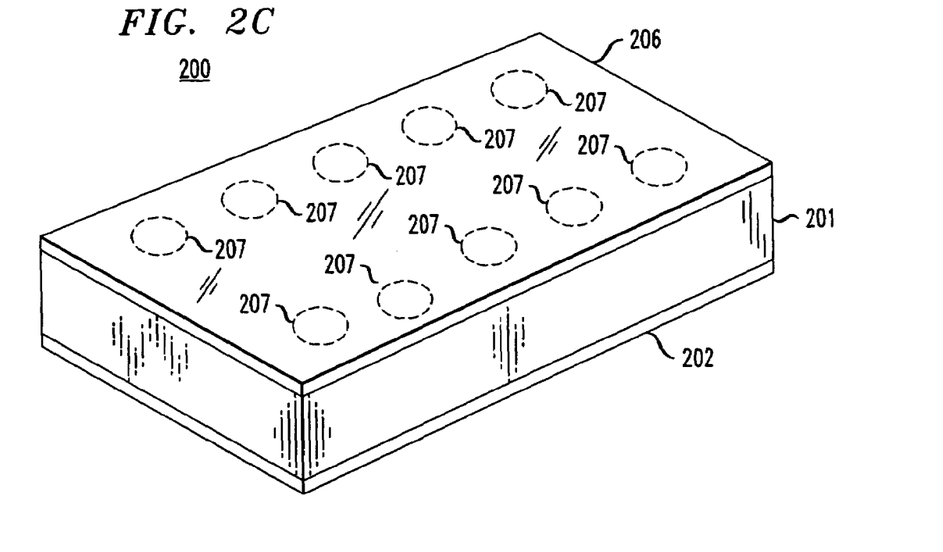
FIG. 2C is another perspective view of the electrically actuated liquid dispenser in accordance with an illustrative embodiment.

FIG. 2C is another perspective view of the liquid dispenser 200 in accordance with an illustrative embodiment. In particular, FIG. 2C depicts the second side of the dispenser 200. The dispenser 200 includes the second layer 206 disposed thereover. As with first layer 202, the second layer 206 is depicted as being transparent to facilitate description of the present embodiment. This layer is not necessarily transparent.

Shown in dashed lines, a plurality of second openings 207 are provided in the substrate 201 as shown. Each opening 207 is at the opposite end of the reservoir from its respective first opening 203. The shape of each of the second openings 207 is substantially identical to the shape of its respective first opening; in the present embodiment circular.

The second layer 206 is usefully deformable and hydrophilic. The former characteristic fosters the application of pressure to the liquid in each reservoir; and the latter characteristic is useful to prevent the absorption of any oil in the liquid material in the reservoir.

Figure 2D:
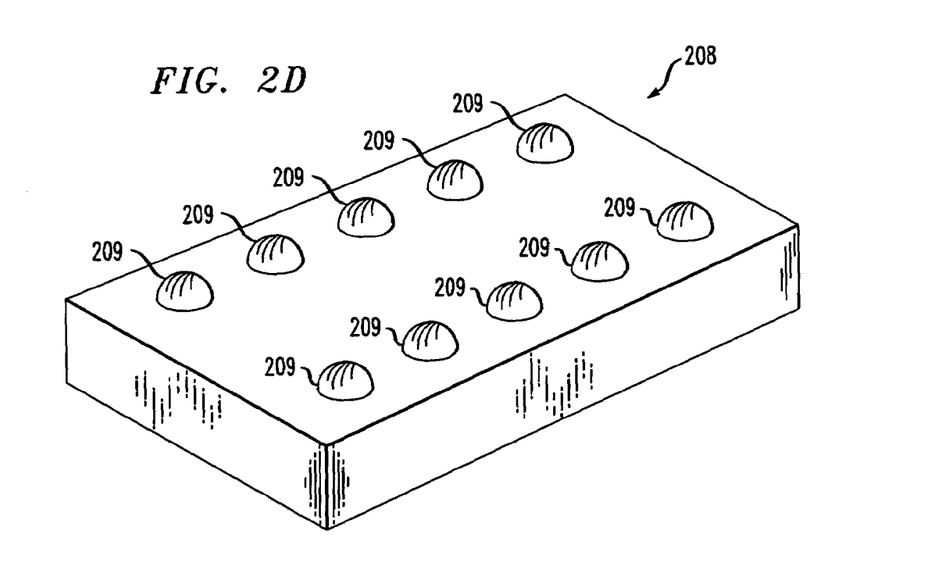
FIG. 2D is a perspective view of a pressure actuator in accordance with an illustrative embodiment.

FIG. 2D is a perspective view of a pressure applicator 208 in accordance with an illustrative embodiment. The pressure applicator 208 includes a plurality of protrusions 209 disposed thereover. The protrusions 209 are shaped to engage the second openings 207 and to press the second layer 206 into the second openings 207. In particular, the pressure applicator 208 is disposed over the second layer 206 of the dispenser 200 with the protrusions 209 of a size and spacing to be aligned with the second openings 206. For example, the protrusions 209 of an embodiment are hemi-spherical in shape, have a diameter that is slightly less than the second openings 207 and have a spacing that is substantially the same as the center-to-center spacing of the second openings 207.

As described more fully herein, after the pressure applicator 208 is aligned with the dispenser 200, a mechanical force from a clamp or other source presses the protrusions 209 into the second openings and creates pressure in the respective reservoirs. In accordance with an embodiment, the pressure from the protrusions, in combination with the heating elements 204 ruptures the first layer 202 over the selected first opening(s) 203 causing the liquid in the reservoir to be released under pressure.

FIGS. 3A-3G are cross-sectional views of a method of fabricating electrically actuated/addressable liquid dispensers in accordance with an illustrative embodiment.

Figure 3A:
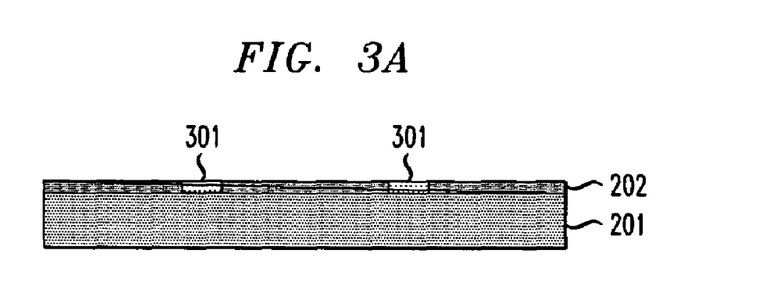
FIGS. 3A-3G are cross-sectional views of method of fabricating an electrically actuated liquid dispenser in accordance with an illustrative embodiment.

FIG. 3A shows the substrate 201 having the first layer 202 disposed thereover. As noted previously, the substrate may be silicon and the first layer 202 may be a negative photoresist such as the polymer SU-8. The first layer 202 is spun-on to the substrate 201 by standard techniques. In a representative embodiment, the first layer 202 (SU-8) has a thickness of approximately 2.0 μm to approximately 10.0 μm and is subjected to a softbake at approximately 65° C. for approximately 2.0 minutes and at approximately 95° C. for approximately 5.0 minutes.

Next, the first layer 202 is patterned, leaving a portion 301 unexposed to the light. A post exposure bake (PEB) step is carried out at approximately 65° C. for approximately 1 minute followed by heating at approximately 95° C. for approximately 2 minutes. As will be readily apparent to one of ordinary skill in the art, the unexposed portion 301 of the first layer 202 is rendered structurally/mechanically weakened. This weakening of the portion 301 fosters the breaking or rupturing of the first layer 202 and the release of liquid material.

It is noted that while the mechanical weakening of at least a part of the first layer 202 is useful in improving atomization when the liquid is released, it is not essential to ensure release of the liquid material. Thus, the actuation by the heating elements 204 or other device could be carried out without first mechanically weakening the first layer 202.

Figure 3B:
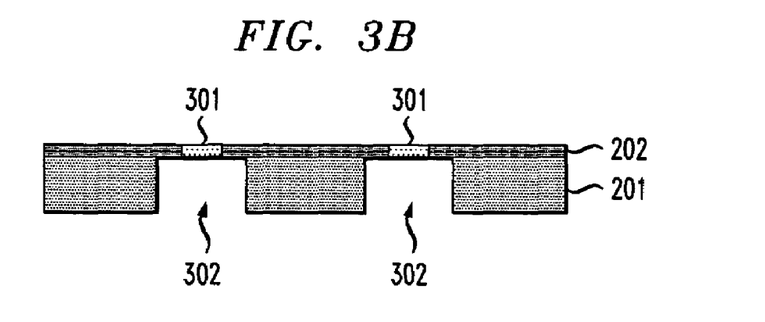

FIG. 3B shows the formed reservoirs 302 in the substrate 201. The reservoirs 302 are formed by micromachining techniques known to those skilled in the art. For example, in an illustrative embodiment, the reservoirs are fabricated by application of a suitable photoresist, which is patterned to expose openings for the reservoirs. In an embodiment, the resist is SPR220-7 resist provided commercially by Shipley Company, LLC of Marlborough, Mass., USA and is applied at a thickness of approximately 10.0 μm. After patterning using a mask to define reservoir openings, the resist is baked at approximately 110° C. for approximately 60 minutes to suitably harden the resist.

After the resist is hardened, the reservoirs 302 are formed a deep reactive etching (DRIE) process. As is known to those skilled in the microelectromechanical systems (MEMS) arts, DRIE etching provides a comparatively highly anisotropic etch of a material. Thus, the reservoirs 302 can have a comparatively large aspect ratio. The DRIE process may be a cryogenic etch or a time multiplexed or pulsed etching method (known as the Bosch method). As these DRIE methods are known to those skilled in the art, details are omitted to avoid obscuring the description of the embodiments. After the etching is completed, the resist is removed by standard technique.

Figure 3C:
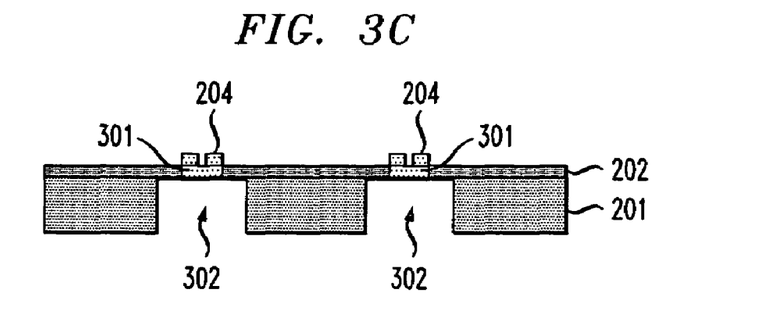

FIG. 3C shows the fabrication of the heating elements 204 in accordance with an illustrative embodiment. A layer of metal is evaporated, which is illustratively titanium/gold (Ti/Au), at a thickness of approximately 0.5 μm to approximately 1.5 μm. Next, photoresist (e.g., approximately 1.6 μm of Shipley 3612) is applied and patterned using a mask to define the heating elements 204. The heater pattern is then wet etched and the resist is removed, leaving the heating elements 204 with pads 205 (not shown in FIG. 3C). In other embodiments, the heater pattern (e.g., Ti) could be etched using known dry-etching techniques.

Figure 3D:
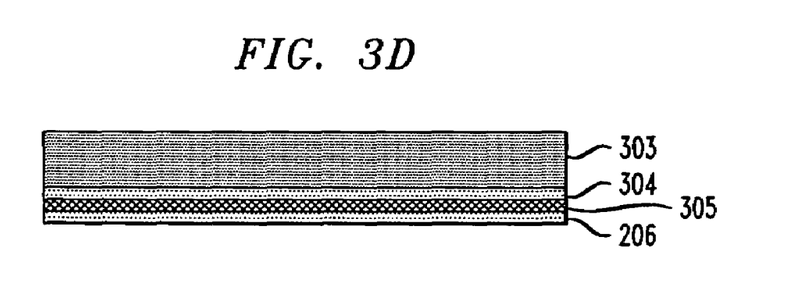

FIG. 3D shows the fabrication of the second layer 206 in accordance with an illustrative embodiment. The method includes providing a first adhesion layer 304 over a substrate 303. In an embodiment, the layer 304 is Poly Di-Methyl Siloxane (PDMS) and the substrate is silicon. After the layer 304 is deposited, a layer 305 is deposited and the (second) layer 206 is deposited thereover. Iluustratively, the layer 305 is polyimide and the layer 206 is PDMS. The layer of polyimide 305 is substantially compliant and allows for the separation of the layer 206 from the substrate 303.

After the layer 206 is deposited, a plasma treatment is undertaken to render the layer 206 of PDMS substantially hydrophilic as desired. In an embodiment, a 100 W oxygen plasma step is carried out. The layers 305 and 206 are then removed for use in subsequent steps described herein. Notably, the substrate may be reused for fabrication of other second layers 206, with the layer 304 of PDMS again forming the first layer of the stack.

Figure 3E:
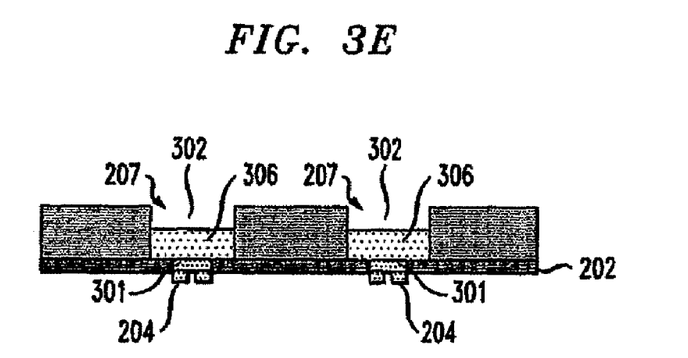

FIG. 3E shows the reservoirs 302 with liquid 306 disposed therein. The liquid 306 may be the alcohol/oil liquid described previously. The liquid 306 may be provided in the reservoirs 302 using a micropipette or other suitable method in the fabrication sequence. For example, liquid 306 may be disposed in the reservoirs 302 with known inkjet spitters used to fill DNA microarrays.

Figure 3F:
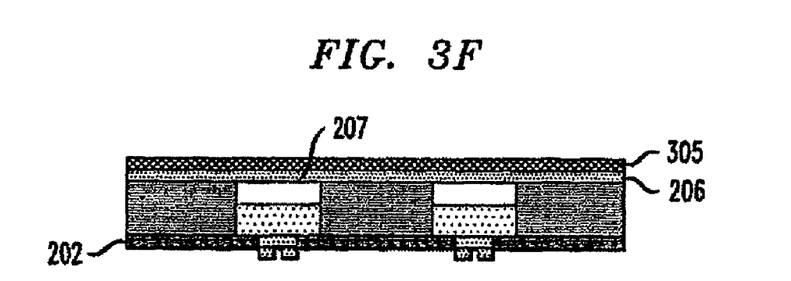

FIG. 3F layers 305 and 206 fabricated as described in connection with FIG. 3D and after transfer to the substrate 201. In illustrative embodiments, layers 206 and 305 together are adhered to the substrate 201 and over the (second) openings 207, with layer 206 in contact with the substrate 201. Layer 305 is then removed by a peeling step.

The fabrication sequence of FIGS. 3A-3F is usefully carried out at wafer scale, providing a large number of reservoirs and heating elements in contact therewith. The wafer may then be diced by known technique and liquid dispensers having one or more reservoirs provided. Likely, an array of reservoirs would be provided, each having a heating element disposed over the first opening and a protrusion from a pressure actuator disposed over the second opening.

Figure 3G:
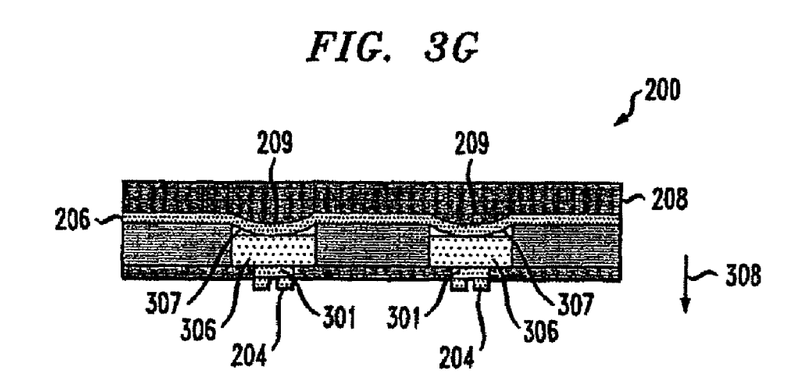

FIG. 3G shows the assembled dispenser 200 in accordance with an illustrative embodiment. The cross-sectional view shows the pressure applicator 208 with protrusions 209 pressing a portion 307 of the second layer 206 into the reservoir 302 thereby creating pressure on the liquid material 306. When the portion of the first layer 202 beneath the heating element 204 breaks, the liquid is released in a direction 308.

Figure 4:
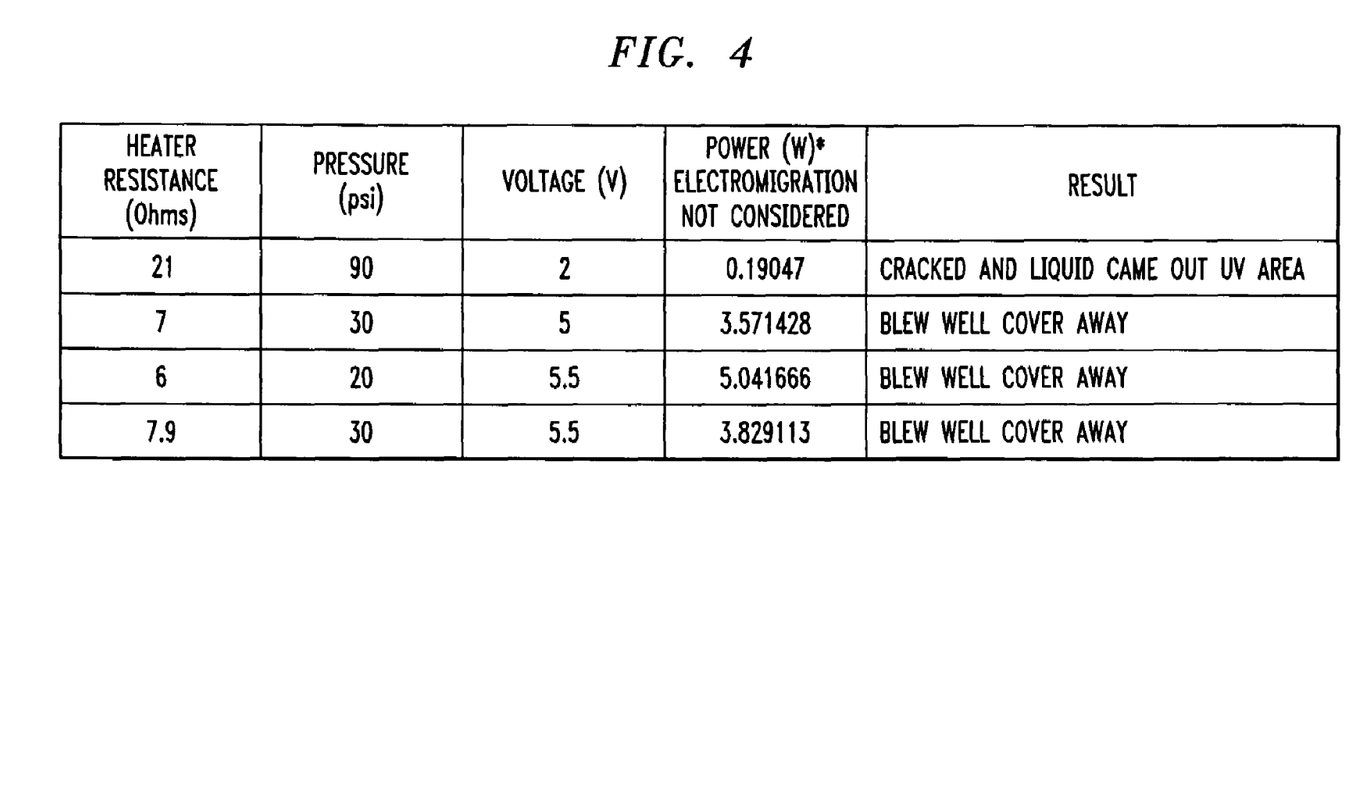
FIG. 4 is a tabular representation of resistance and power of heating elements in accordance with an illustrative embodiment.

FIG. 4 is a tabular representation of tests performed on representative liquid dispensers. The resistance of the heating elements, the pressure, the applied voltage and the power are shown in tabular form. Also, comments showing the result of the combination of heat and pressure are provided. It is emphasized that the results of FIG. 4 are merely illustrative of an embodiment and are in no way limiting.

Figure 5:
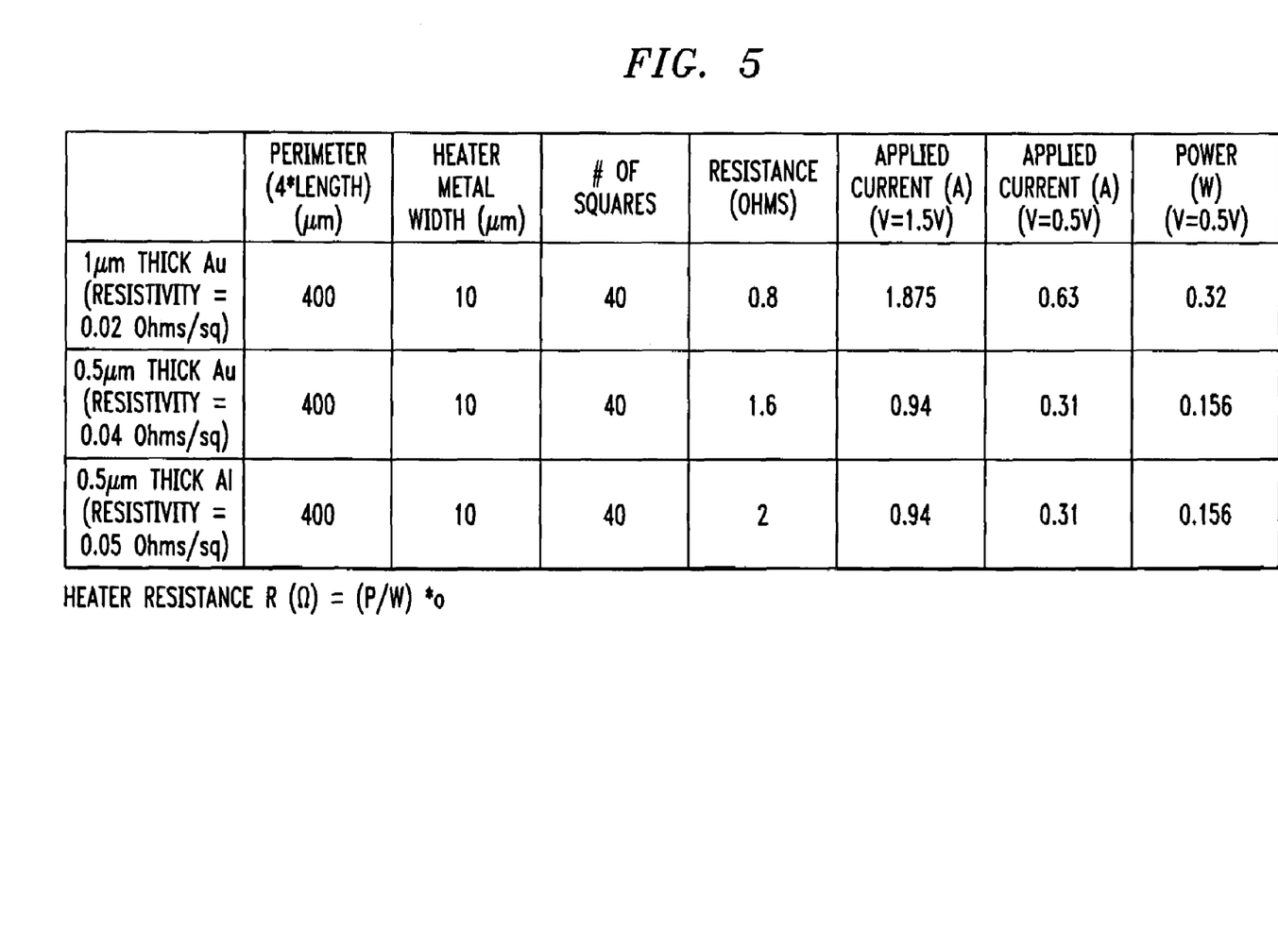
FIG. 5 is a tabular representation of resistance of heating elements in accordance with an illustrative embodiment.

FIG. 5 is a tabular representation of illustrative materials and thicknesses thereof for use as heating elements. The table shows the perimeter of the heating elements, the width of the metal traces of the heating elements and the power provided for combinations voltage, material and dimensions. It is emphasized that the results of FIG. 5 are merely illustrative of an embodiment and are in no way limiting.

In connection with illustrative embodiments, an electrically actuated liquid dispenser, an electrically addressable liquid dispenser and an electronic device are described. One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

The invention claimed is:

1. An electrically actuated liquid dispenser, comprising:
   a reservoir having a first layer disposed over a first opening and a second layer disposed over a second opening;
   a liquid material disposed in the reservoir;
   a heating element disposed over at least a portion of the first layer disposed over the first opening; and
   a pressure applicator disposed over at least a portion of the second layer disposed over the second opening, wherein the heating element is adapted to mechanically weaken the portion of the first layer causing the first layer to break and to release the liquid material under pressure.

2. An electrically actuated liquid dispenser as claimed in claim 1, wherein the liquid material is a scented material.

3. An electrically actuated liquid dispenser as claimed in claim 1, wherein the second layer is a hydrophilic material and the liquid material includes an oil.

4. An electrically actuated liquid dispenser as claimed in claim 1, wherein the first layer is a negative photoresist layer.

5. An electrically actuated liquid dispenser as claimed in claim 1, wherein the heating element is a resistive heating element.

6. An electrically addressable liquid dispenser, comprising:
   a plurality of reservoirs, each reservoir having a first layer disposed over a first opening and a second layer disposed over a second opening;
   a liquid material disposed in each of the reservoirs;
   a plurality of heating elements, each heating element being disposed over a respective one of the first openings and being in contact with at least a portion of the first layer disposed over the respective first openings; and
   a pressure applicator disposed over each of the second openings and being in contact with the second layer.

7. An electrically addressable liquid dispenser as claimed in claim 6, wherein the liquid material is a scented material.

8. An electrically addressable liquid dispenser as claimed in claim 7, wherein the scented liquid material of at least two of the plurality of reservoirs have different scents.

9. An electrically addressable liquid dispenser as claimed in claim 6, wherein each of the heating elements is a resistive heating element.

10. An electrically addressable liquid dispenser as claimed in claim 9, wherein each heating element is connected to driver electronics, which are adapted to provide current to at least one selected heating element causing the first layer over the respective first opening to break and to release the liquid material under pressure.

11. An electrically addressable liquid dispenser as claimed in claim 9, wherein each heating element is connected to driver electronics, which are adapted to provide current to at least two selected heating elements causing the first layer over respective first openings to break and to substantially simultaneously release respective liquid materials under pressure.

12. An electrically addressable liquid dispenser as claimed in claim 6, wherein each second layer is a hydrophilic material and the liquid material in each of the reservoirs includes an oil.

13. An electrically addressable liquid dispenser as claimed in claim 6, wherein each first layer is a negative photoresist layer.

14. A portable electronic device, comprising:
   an electrically addressable liquid dispenser, which includes
      a plurality of reservoirs, each reservoir having a first layer disposed over a first opening and a second layer disposed over a second opening;
      a liquid material disposed in each of the reservoirs;
      a plurality of heating elements, each heating element being disposed over a respective one of the first openings and being in contact with at least a portion of the first layer disposed over the respective first openings; and
      a pressure applicator disposed over each of the second openings and being in contact with the second layer.

15. A portable electronic device as claimed in claim 14, wherein the liquid material is a scented material.

16. A portable electronic device as claimed in claim 15, wherein the scented liquid material of at least two of the plurality of reservoirs have different scents.

17. A portable electronic device as claimed in claim 14, wherein each of the heating elements is a resistive heating element.

18. A portable electronic device as claimed in claim 17, wherein each heating element is connected to driver electronics, which are adapted to provide current to at least two selected heating elements causing the first layer over respective first openings to break and to substantially simultaneously release respective liquid materials under pressure.

19. A portable electronic device as claimed in claim 14, wherein the device is one of: a mobile telephone, a personal digital assistant (PDA), a portable computer, a portable audio device, a portable video device, a portable gaming device.

20. A portable electronic device as claimed in claim 17, wherein each heating element is connected to driver electronics, which are adapted to provide current to at least one selected heating element causing the first layer over the respective first opening to break and to release the liquid material under pressure.

* * * * *

UNITED STATES PATENT AND TRADEMARK OFFICE
CERTIFICATE OF CORRECTION

PATENT NO. : 7,715,699 B2
APPLICATION NO. : 11/502276
DATED : May 11, 2010
INVENTOR(S) : Lamers et al.

It is certified that error appears in the above-identified patent and that said Letters Patent is hereby corrected as shown below:

Title Page, Item (73) Assignees: should read as follows:
Avago Technologies Wireless IP (Singapore) Pte. Ltd., Singapore (SG)
The Boards of Trustees of the Leland Stanford Junior University,
1705 El Camino Real, Palo Alto, California 94306-1106

Signed and Sealed this

Fourteenth Day of September, 2010

David J. Kappos
*Director of the United States Patent and Trademark Office*